United States Patent
Koslow et al.

(10) Patent No.: US 6,607,672 B2
(45) Date of Patent: Aug. 19, 2003

(54) APPARATUS AND METHOD FOR COMBINED USE OF ULTRAVIOLET AND OZONE IN APPLIANCES

(75) Inventors: Evan E. Koslow, Weston, CT (US); Lawrence S. Walters, Jr., Woodbridge, CT (US)

(73) Assignee: Koslow Technologies Corp., Orange, CT (US)

( * ) Notice: Subject to any disclaimer, the term of this patent is extended or adjusted under 35 U.S.C. 154(b) by 3 days.

(21) Appl. No.: 10/001,209

(22) Filed: Oct. 31, 2001

(65) Prior Publication Data

US 2003/0080068 A1 May 1, 2003

(51) Int. Cl.⁷ .................................................. C02F 1/32
(52) U.S. Cl. ........................ 210/748; 210/760; 210/764; 222/146.6
(58) Field of Search ................................. 210/748, 760, 210/764; 222/146.6

(56) References Cited

U.S. PATENT DOCUMENTS 5,474,748 A * 12/1995 Szabo
5,709,799 A * 1/1998 Engelhard
6,464,868 B1 * 10/2002 Korin

* cited by examiner

Primary Examiner—Betsey Morrison Hoey
(74) Attorney, Agent, or Firm—Shirley S. Ma

(57) ABSTRACT

A method and apparatus for treating an oxygen containing gas (generally air) and/or water in an appliance such as a refrigerator washing machine, dryer or dishwasher with ozone so as to disinfect the water used within the appliance and use the ozone in the air to disinfect the interior space and the contents of the appliance. Arrangements may be made to provide disinfected water on demand. The ozone containing gas is provided when needed, or in the case of a refrigerator, at a time of the day when the refrigerator is not generally in use. The generator may include a source of ultraviolet radiation, a plenum for the air and a plenum for the water. The plenum for the water may be in the form of a tube which is transparent to ultraviolet. The diameter of the tube is preferably selected so that plug flow of water through the tube occurs. The ozone containing air and the disinfected water may be provided to a location remote from the appliance.

50 Claims, 1 Drawing Sheet

APPARATUS AND METHOD FOR COMBINED USE OF ULTRAVIOLET AND OZONE IN APPLIANCES

BACKGROUND OF THE INVENTION

1. Field of the Invention

This application relates to the treatment of air and water with ozone in appliances to effectively disinfect the air and/or water. More particularly, it relates to apparatus and methods to efficiently and effectively treat air and water in appliances such as refrigerators, dishwashers, and washing machines in a cost efficient manner.

2. Prior Art

The disinfection properties of ozone are well documented. There have been suggestions that ozone be used in appliances to assist in suppressing the growth of bacteria and fungus, thus minimizing decay and suppressing the generation of unpleasant odors.

There is a need for an apparatus that can be applied to an appliance economically and effectively to use ozone to suppress bacterial growth in both water and air. Further, the apparatus should be capable of producing water with reduced microbiological content, on demand, without the need to have a large storage tank, in which water may be held for long periods of time and in which bacteria may grow prior to the demand for the water.

SUMMARY OF THE INVENTION

It is an object of the present invention to provide an apparatus that conveniently provides disinfected water and a supply of ozone-enriched air, which can be used to suppress subsequent biological activity or can be used to control biological growth within the appliance.

It is a further object of the invention to provide disinfected water to a number of devices which may require it, on demand.

It is another object of the invention to provide air having the ability to suppress biological activity on a periodic basis, to an appliance such as in a refrigerator or washing machine, and possibly to a food storage space in the same general area as the appliance.

The invention is directed to an appliance capable of receiving an oxygen-containing gas and water, the appliance including an apparatus for treating the oxygen containing gas and water. It is also directed to a system for use in such an appliance. The apparatus comprises a source of ultraviolet radiation; a first input associated with the source for receiving water to be exposed to the radiation; a first output for the water that has been exposed to the radiation; a second input associated with the source for receiving the oxygen containing gas to be exposed to the radiation so that ozone is formed in the gas; and a second output for the gas containing the ozone. It should be noted that while ultraviolet light produces ozone, ultraviolet light may also produce other chemicals or reactive species that are also effective as disinfectants. However, we refer to all of these disinfecting species as "ozone" herein.

Preferably, the oxygen containing gas is air. The source of ultraviolet radiation may be a mercury filled electrical bulb. The appliance may be a refrigerator, a dishwasher, a clothes washing machine, a clothes dryer, and a clothes washer/dryer. The apparatus may be mounted inside or outside the appliance.

The appliance may further comprise a controller for controlling the source of ultraviolet radiation so that the source is turned on when water begins to flow into the first input, and remains on for a fixed period of time after water ceases to flow into the input, so that water which has flowed into the input but has not yet flowed out of the output is fully treated. The controller may periodically cause the source of ultraviolet radiation to be turned on to periodically ensure treatment of the water held in the device.

The appliance may further comprise a storage vessel for storing disinfected (and chilled) water. The storage vessel may be pressurized so that disinfected water can be dispensed on demand.

The appliance may further comprise a pressure or flow sensor for detecting a drop in pressure or start of flow at the first output, and a flow activating apparatus for activating flow of water into the first input when a drop in pressure or start of flow is detected by the pressure or flow sensor.

The appliance may further comprise a sensor for detecting ultraviolet radiation produced by the source; and the flow activating apparatus may activate the flow of water into the first input only when both the drop in pressure or flow of water, and detection of ultraviolet radiation by the sensor simultaneously occur.

The appliance may further comprise a filter apparatus disposed to filter water of certain chemical or particulate contaminants prior to the water entering the first input.

The apparatus may further comprise a housing, the source of ultraviolet radiation being disposed in the housing; a first plenum through which water may be caused to flow from the first input to the first output, the first plenum being sized, shaped, and positioned so that water in the first plenum is exposed to the ultraviolet radiation to a degree sufficient to suppress biological activity in the water; and a second plenum through which air may be caused to flow from the second input to the second output, the second plenum being sized, shaped, and positioned so that when the gas is in the second plenum, the gas is exposed to the ultraviolet radiation to a degree sufficient to form ozone in the gas. The first plenum and the second plenum may be cylindrical and coaxial.

The apparatus may further comprise a tube through which the water flows from the first input to the first output, the tube having characteristics that permit the ultraviolet radiation to suppress biological activity in the water; and a plenum through which gas may be caused to flow from the second input to the second output, the plenum being sized, shaped, and positioned so that when the gas is in the plenum, the gas is exposed to the ultraviolet radiation to a degree sufficient to form ozone in the gas. The tube is substantially transparent to the ultraviolet radiation and may be formed of tetraflouroethylene or quartz.

The appliance may further comprise at least one gas conducting means for conducting the ozone containing gas to a location remote from the appliance, the location being, for example, a storage area for food. The appliance may further comprise a bubbler to produce ozone-enriched water that can be used as a disinfectant, as a bleach, or to control re-growth of bacteria and other microbiota.

The invention is also directed to a method for reducing biological activity in an appliance, which is capable of receiving an oxygen containing gas and water. The method comprises generating ultraviolet radiation; exposing the oxygen containing gas and the water in the appliance to the radiation to suppress biological activity in the water and to generate ozone in the gas. The exposing of the gas and the water may occur simultaneously. Preferably, the gas is air, but it could be other fluids.

In the case of the appliance being a refrigerator, the method further comprises circulating the gas containing the ozone through the food containing compartments of the refrigerator, including circulating the gas periodically, possibly for a short period of time each day, such as when the refrigerator is not generally in use, as for example, during night time hours or during periods of time when the inhabitants are working. For example, the gas may be circulated for a period of time between thirty seconds and two hours once every day.

The source of ultraviolet radiation may be turned on when water is to be disinfected for use. In that case, it is not necessary to circulate the gas.

The method may further comprise conducting the ozone containing gas to a location remote from the appliance, such as to a food storage space. A bubbler may be used to produce ozone-enriched water that can be used as a disinfectant, as a bleach, or to control re-growth of bacteria and other microbiota.

BRIEF DESCRIPTION OF THE DRAWING

The foregoing aspects and other features of the present invention are explained in the following description, taken in connection with the accompanying drawing, wherein.

DETAILED DESCRIPTION OF THE PREFERRED EMBODIMENTS

Figure 1:
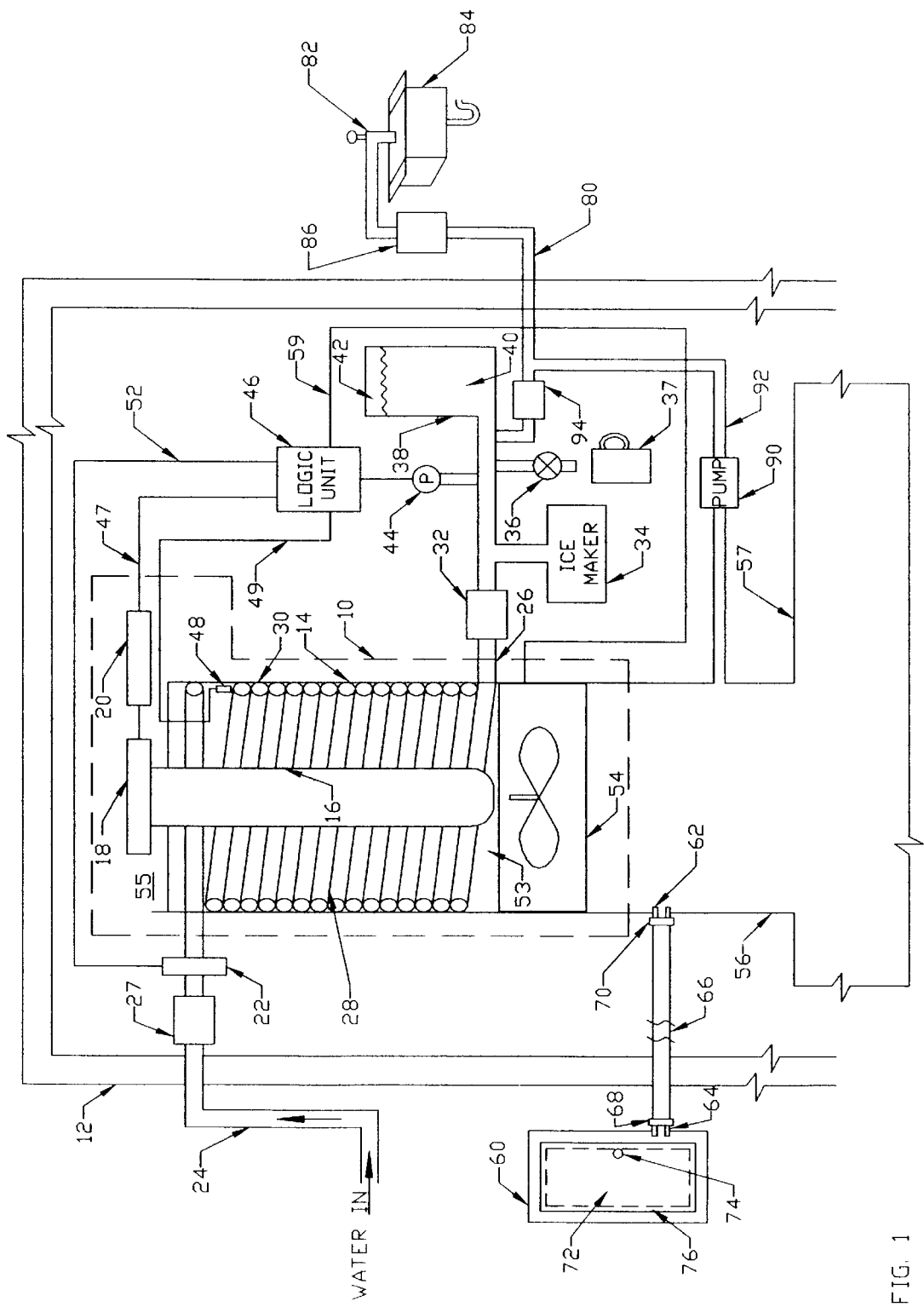
FIG. 1 is a schematic diagram of an apparatus in accordance with the invention.

Referring to FIG. 1, there is shown a cross sectional view of an apparatus 10 incorporating features of the present invention. Although the present invention will be described with reference to the embodiment shown in the drawings, it should be understood that the present invention can be embodied in many alternate forms of embodiments. In addition, any suitable size, shape or type of elements or materials could be used.

In FIG. 1, an embodiment of the invention includes an apparatus 10 which may be used to provide disinfected water and air carrying a disinfecting agent or agents in a refrigerator represented by a housing 12 in which apparatus 10 is disposed. As more fully described below, housing 12 may also be that of a dishwasher or a clothes dryer or other "white goods" treatment apparatus wherein air and water are used. Alternatively, apparatus 10, instead of being mounted within housing 12, may be closely connected to housing 12, as for example by being mounted on the outside thereof as more fully described below.

Apparatus 10 includes an ozone generator 14 having a source of ultraviolet energy such as an elongate mercury filled bulb 16 in which an electrical discharge is created. Bulb 16 is supported by a base 18 to which power is supplied by a power supply 20 containing, for example, a ballast and being of a type well-known in the art. Bulb 16 provides ultraviolet energy in the 154 nanometer range, which is well suited for killing or suppressing the growth of microorganism such as bacteria, fungi and viruses in water and for the generation of ozone in air to kill or suppress these microorganisms. A corona discharge or other ozone generating means may be arranged to provide supplemental production of ozone. However the use of ultraviolet radiation allows the convenient and economical disinfecting of both the liquid and gas media in a single apparatus and in a small device with modest total power consumption.

An electrically operated water shut off valve 22 controls the flow of water from a water supply line 24 to a water output line 26. Line 24 may have disposed along its length a filter 27 to remove chemical (organic and inorganic) and other contaminants. The filter 27 may be a carbon block filter of a type well known in the art of water purification, such as, for example, a carbon block filter manufactured by KX Industries, L.P. of Orange, Conn., USA. The output side of water shut off valve 22 provides water to a tube 28 which is coiled about the inner surface of a cylindrical housing 30 of ozone generator 14, which may be formed of a metal, and in particular of a metal which acts as a reflector of radiation striking the internal wall of housing 30. Tube 28 is formed of a material such as Teflon® (tetraflouroethylene) or quartz, which is transparent to the ultraviolet radiation produced when bulb 16 is powered by power supply 20. Tube 28 effectively acts as a plenum for water circulated through generator housing 30. Although the use of a coiled tube is advantageous, other geometries for this plenum are possible, including an ultraviolet transparent cylindrical insert for placement in housing 30, the insert having a cylindrical opening for receiving bulb 16.

Regardless of the form of the water plenum, bulb 16 is received in housing 30, the longitudinal axis of bulb 16 and housing 30 lying along the same line. The end of tube 28 not connected to valve 22 is connected to a check valve 32, which prevents the back flow of water should water pressure be lost on water supply line 24.

The output of check valve 32 is connected to several places. Water is supplied to an ice maker 34 of the refrigerator 12. Water is also supplied to a manually operated water valve 36 which the consumer may use to obtain chilled water to, for example, fill a drinking glass or mug 37 or other suitable receptacle, the water being for applications such as cooking, or simply for drinking. It will be understood that the water may, at some point, pass through a region in the refrigerator where the temperature is below room temperature, but above freezing, so that the water is suitably chilled for drinking. For example, if located within housing 12, apparatus 10 will be placed so that it is in a refrigerated part of the refrigerator other than a freezer.

Also attached to the output of check valve 32 is a water accumulator tank 38 which has a quantity of water 40 often located below an air space 42. Air in air space 42 is compressed by the pressure of water 40, thus providing a source of chilled water instantaneously upon the opening of the valve 36 or when water is demanded by icemaker 34. Tank 38 may be of a small size, such as for example one half liter, and may be removable for occasional cleaning, with the use of appropriate check valves and automatic shut off valves. Apparatus 10 may also be disabled automatically during such cleaning operations. It may be larger if it is desired to obtain a larger quantity of water before the pressure drops and water shut off valve 22 opens. However, bacterial growth will generally not be a significant issue due to the fact that only disinfected water is allowed to reach tank 38.

Also connected to the output of check valve 32 is a pressure sensor 44 which detects any drop in pressure at the output of check valve 32. For example, if icemaker 34 demands water, or the consumer demands drinking water upon opening valves 36, water will be supplied instantly from the accumulator 38. However, the pressure in the line connecting all of these items will immediately drop. When this pressure drop occurs, pressure sensor 44 provides an output to a logic unit 46. Logic unit 46 in turn provides a signal on a line 47, which is connected to and turns on power supply 20 to activate bulb 16 to provide ultraviolet radiation.

An ultraviolet sensor 48 is provided within housing 30 to sense ultraviolet radiation produced by bulb 16, thus indicating that bulb 16 has in fact been turned on. It is only when an output signal from pressure sensor 44, and an output signal from ultraviolet sensor 48 (provided on line 49) have both been received, that logic unit 46 provides a signal on a line 52 to open water supply valve 22, thus allowing water from water supply line 24 to be fed into the system. Since it takes some time for the water to travel along the coils of line 28 from the input side of housing 30 to the output side, and the water will be irradiated by ultraviolet energy during this travel, the water provided at the output of check valve 32 will be disinfected water. In other words, plug flow of the water occurs, without substantial mixing of the water as it traverses tube 28, at a speed slow enough so that, taking into account time for bulb 16 to turn on after receiving the appropriate signal from logic unit 46, and the time needed to treat the water, only disinfected water will ever exit from apparatus 10.

Logic unit 46 is advantageously programmed so that even when the flow of water has stopped, there is a delay until power to bulb 16 is turned off. This permits water, which has just entered housing 30, to be disinfected, even though the flow of water has stopped and the pressure sensed by pressure sensor 44 has returned to normal. In addition, logic unit 46 can periodically activate power supply 20, thus periodically turning on bulb 16 and irradiating the water in tube 28 for a sufficient length of time to be sure that the water remains fully disinfected.

The dimensions of housing 30, bulb 16 and tube 28 are chosen so that there is an annular space between bulb 16 and tube 28 which forms an air plenum 53. A fan 54, when operating, causes air to be pulled in from the top region 55 of housing 30, circulated past bulb 16, and then propelled into a duct 56. Duct 56 conducts air to at least one food containing compartment 57 of refrigerator 12. A separate duct (not shown) may be provided to conduct air back from food containing compartment 57 to the top region 55 of housing 30.

Advantageously, fan 54 may be turned on periodically, by a signal from logic unit 46 on an electrical line 59, at the same time as a signal is provided on line 47 to turn on power supply 20 to illuminate bulb 16. When this simultaneous operation occurs, ozone is generated in the air passing through plenum 53. This air, provided to the food containing compartments, suppresses the growth of odor causing and food spoiling microorganisms such as bacteria and fungus, and viruses. Fan 54 and bulb 16 may remain on for a period of time sufficient to activate whatever degree of treatment is desired, ranging from periodic activation, activation during the late evening hours to achieve a "disinfection treatment cycle" or continuously whenever the refrigerator main circulation fan is activated. In the latter case, a separate fan 54 may not be needed, if the air flow path through the refrigerator is designed so that an adequate fraction of the air passes through plenum 53.

It will be recognized that it is advantageous to cycle bulb 16 and fan 54 on at times of the twenty four hour day when it is less likely that the refrigerator will be opened for the purpose of individuals gaining access to the food containing compartments. This is because even a small concentration of ozone can be quite irritating to the users of the refrigerator, although generally not harmful.

In a variation of the invention, ozone generator 10 is mounted externally of refrigerator housing 12. In this embodiment, a complex logic unit 46 is not required. Power supply 20 may be operated continuously, thus continuously illuminating bulb 16 and providing a source of ultraviolet radiation at all times. Since the ozone generator is mounted externally of the refrigerator, there is no excess heat generated to reduce the efficiency of the refrigerator. While a logic unit is not required, a timer is still required to periodically provide electrical power to fan 54 so that ozone is circulated to the food containing compartments of the refrigerator only at selected times, as described above.

It is been found that ozone generation in the environment of a refrigerator is reduced by the presence of high humidity. However, the hydrolyzed radicals produced instead of ozone are, to a first order, as effective as ozone in reducing unwanted biological activity. Thus, whether it is ozone or free radicals that are produced, they are still effective in reducing bacterial and fungal growth, thus suppressing the production of undesirable odors and helping to ensure that food products are kept fresh.

As mentioned above, the appliance may be other than a refrigerator. The appliance may be, for example, a clothes washing machine, a clothes dryer or a combination washer/dryer with an ozone generator of the type such as ozone generator 10 contained internally or mounted externally thereto. The water supplied to wash the clothes may be disinfected by the apparatus and method of the invention. Additionally, if a small amount of the ozone produced is drawn or injected into the water, that is it is sparged into the water, (by using a pump as illustrated below, or by using a Venturi arrangement (not shown) wherein the flow of water generates a low pressure region to draw the ozone containing air into the water) the need for the addition of bleach may be greatly reduced or eliminated due to the bleaching action of the ozone. Further, the clothes may be subject to an air stream containing a small amount of ozone, to assist in killing bacteria, thus providing a fresh scent to the clothing. Air from a duct similar to duct 56, can provide this ozone containing air. Heated air, which is used in dishwashers, may in a similar fashion, also be made to contain a small amount of ozone to kill microorganisms. In this latter case, since drying air is sometimes vented to the indoor atmosphere, it may be necessary to provide an apparatus for destroying the ozone. A timer may be used to turn on the ozone generator so as to supply ozone to the water or air as required. In the case of drying, the ozone generator may operate continuously during the drying process, but may be caused to stop operating prior to the end of the cycle to allow ozone to dissipate in accordance with its natural breakdown into oxygen.

The appliance in which ozone generator 10 is located may also be a clothes dryer. The air in the dryer may be circulated and may be made to contain a small amount of ozone to kill any bacteria or other microorganisms which remain on the clothes. In this latter case, since drying air is generally vented from the dryer to the outside environments, it is not necessary to provide an apparatus for destroying the ozone. When such an ozone destroying apparatus is required, any of the devices well-known in the art may be used.

In accordance with the invention, it is also possible to provide ozone from apparatus 10 to one or more food containing compartments, containers, or any other food storage means external to the appliance or refrigerator housing 12, such as a pantry or a food containing cabinet 60 to assist in suppressing the growth of bacteria and fungus, thus minimizing decay and minimizing the generation of unpleasant odors in the food or the item in which it is stored. If apparatus 10 is mounted externally to, for example, the back of housing 12, this may be accomplished by use of a fitting 62 on duct 56 (a portion of duct 56 being disposed external to housing 12) and a fitting 64 associated with cabinet 60. Fittings 62 and 64 should be air tight and connected by a suitable air tight pipe or hose 66 having mating fittings 68 and 70 on the ends thereof, the hose or pipe being formed of a material resistant to the ozone to which it is exposed.

If cabinet 60 is a conventional kitchen cabinet having a door 72 and a handle 74, retention of ozone may be enhanced by providing a seal 76 comparable to, for example, a weather stripping to at least partially seal cabinet 60.

It will be understood that while a single cabinet 60 has been shown, it is in principle possible to have several such cabinets receive small amounts of ozone from apparatus 10 using a similar arrangement to that illustrated. In this case, a supplemental ozone generator, as discussed above, may be required to produce adequate quantities of ozone.

As also discussed above, ozone may be provided periodically, such as times when most individuals in a household where the appliance is located are sleeping. Alternatively, it can be provided periodically when the main circulation fan in, for example, a refrigerator is activated, as discussed above.

It will be recognized that connecting to one or more food containing cabinets 60 may be accomplished most easily when a portion of duct 56 is external to housing 12 and one or more fittings 62 are provided. However, it is also possible to provide ozone to external locations when apparatus 10 is located within housing 12, provided that suitable connections are maintained between fittings on apparatus 10 and fittings on the wall of housing 12. In that case, a suitable hose, such as hose 66, is used between a fitting on the outside of housing 12 and a food cabinet such as cabinet 60.

Whether apparatus 10 is mounted externally to housing 12, or is mounted internally and the more complex arrangement discussed above is implemented, whenever a fitting is not connected to a hose which supplies ozone to a location remote from housing 12, a suitable cap is placed over the fitting to prevent ozone from escaping into the environment where the appliance is located.

It will be recognized that other variations and modifications of the invention are possible. For example, apparatus 10 may be sold, along with appropriate hardware, as a separate kit, which may be installed in the field, as an option, provided that appropriate connections and connection lines are provided on appliance 12. Further, if ozone is sparged into the water it will provide a residual disinfecting effect. In this case, it is possible that apparatus 10 may be mounted at a location remote from the appliance.

Whether remote from the appliance or mounted to or within the appliance, apparatus 10 may be a source of disinfected water to be supplied to other locations. For example, a water output line 80, such as a pipe or appropriate hose, may be provided to other locations. These locations may include, for example, a water faucet 82 associated with a utility sink 84 or a spout of a drinking fountain (not shown) so that disinfected water is available at such remote locations. In this case, a separate water temperature control unit 86 (such as a chilling unit for drinking water) may be provided at the remote location. It will be understood that appropriate connection hardware (not shown) similar to that used to remotely supply ozone containing air, as described above, may also be used.

If ozone or ozone-containing air is sparged into the water, such water provided at remote locations will enjoy a residual disinfecting effect. This may be accomplished using a small air pump 90, located along a supply line 92. Line 92 may feed the water output line 80 and may operate when water is supplied to a remote location by line 80. An appropriate check valve 94 assures that water that contains ozone is not directed so as to become drinking water. Thus, water can be supplied to utility sink 84 or another appliance such as from a refrigerator to a washing machine. It will be recognized that a supplemental ozone generator, as mentioned above, may be required within apparatus 10 for such applications where the demand for ozone is particularly high.

It will be understood that various alternatives and modifications to the invention can be devised by those skilled in the art without departing from the invention. Accordingly, the present invention is intended to embrace all such alternatives, modifications and variances which fall within the scope of the appended claims.

What is claimed is:

1. An appliance capable of receiving an oxygen containing gas and water, said appliance including an apparatus for treating said oxygen containing gas and wafer, said apparatus comprising:
   a source of ultraviolet radiation;
   an ultraviolet sensor for sensing ultraviolet radiation from said source;
   a first input associated with said source for receiving water to be exposed to said radiation;
   a first output for said water which has been exposed to said radiation;
   a second input associated with said source for receiving said oxygen containing gas to be exposed to said radiation so that ozone is formed in said gas; and
   a second output for said gas containing said ozone.

2. The appliance of claim 1, further comprising a storage vessel for storing disinfected water.

3. The appliance of claim 2, wherein said storage vessel is pressurized so that disinfected water is provided on demand.

4. The appliance of claim 1, further comprising a filter apparatus disposed to filter water of contaminants prior to said water entering said first input.

5. The appliance of claim 1, wherein said source of ultraviolet radiation is a mercury filed electrical bulb.

6. The appliance of claim 1, further comprising:
   a housing, said source of ultraviolet radiation being disposed in said housing;
   a first plenum through which water may be caused to flow from said first input to said first output, said first plenum being sized, shaped, and positioned so that water in said first plenum is exposed to said ultraviolet radiation to a degree sufficient to suppress biological activity in said water; and
   a second plenum through which air may be caused to flow from said second input to said second output, said second plenum being sized, shaped, and positioned so that when said gas is in said second plenum, said gas is exposed to said ultraviolet radiation to a degree sufficient to form ozone in said gas.

7. The appliance of claim 6, wherein said first plenum and said second plenum are cylindrical.

8. The appliance of claim 6, wherein said first plenum and said second plenum are coaxial.

9. The appliance of claim 1, further comprising:
   a tube through which said water flows from said first input to said first output, said tube having characteristics which permit said ultraviolet radiation to suppress biological activity in said water; and
   a plenum through which gas may be caused to flow from said second input to said second output, said plenum being sized, shaped, and positioned so that when said gas is in said plenum, said gas is exposed to said ultraviolet radiation to a degree sufficient to form ozone in said gas.

10. The appliance of claim 1, wherein said apparatus is mounted inside said appliance.

11. The appliance of claim 1, wherein said apparatus is mounted outside said appliance.

12. The appliance of claim 1, further comprising at least one gas conducting means for conducting said ozone containing gas to a location remote from said appliance.

13. The appliance of claim 1, further comprising at least one water conducting means for conducting said water from said second outlet to a location remote from said appliance.

14. The appliance of claim 1, further comprising means for introducing ozone into said water.

15. An appliance capable of receiving an oxygen containing gas and water, said appliance including an apparatus for treating said oxygen containing gas and water, said apparatus comprising:
- a source of ultraviolet radiation;
- a first input associated with said source for receiving water to be exposed to said radiation;
- a first output for said water which has been exposed to said radiation;
- a second input associated with said source for receiving said oxygen containing gas to be exposed to said radiation so that ozone is formed in said gas;
- a second output for said gas containing said ozone; and
- a controller for controlling said source of ultraviolet radiation so that said source is turned on when water begins to flow into said first input, and remains on for a fixed period of time after water ceases to flow into said input, so that water which has flowed into said input but has not yet flowed out of said output is fully treated.

16. An appliance capable of receiving an oxygen containing gas and water, said appliance including an apparatus for treating said oxygen containing gas and water, said apparatus comprising:
- a source of ultraviolet radiation;
- a first input associated with said source for receiving water to be exposed to said radiation;
- a first output for said water which has been exposed to said radiation;
- a second input associated with said source for receiving said oxygen containing gas to be exposed to said radiation so that ozone is formed in said gas;
- a second output for said gas containing said ozone; and
- a controller for controlling said source of ultraviolet radiation so that said source is turned on when water begins to flow into said first input, and remains on for a fixed period of time after water ceases to flow into said input, so that water which has flowed into said input but has not yet flowed out of said output is fully treated, wherein said gas is air.

17. An appliance capable of receiving an oxygen containing gas and water, said appliance including an apparatus for treating said oxygen containing gas and water, said apparatus comprising:
- a source of ultraviolet radiation;
- a first input associated with said source for receiving water to be exposed to said radiation;
- a first output for said water which has been exposed to said radiation;
- a second input associated with said source for receiving said oxygen containing gas to be exposed to said radiation so that ozone is formed in said gas;
- a second output for said gas containing said ozone; and
- a controller for controlling said source of ultraviolet radiation so that said source is turned on when water begins to flow into said first input, and remains on for a fixed period of time after water ceases to flow into said input, so that water which has flowed into said input but has not yet flowed out of said output is fully treated, wherein said controller periodically causes said source of ultraviolet radiation to be turned on to periodically ensure treatment of said water held in the device.

18. An appliance capable of receiving an oxygen containing gas and water, said appliance including an apparatus for treating said oxygen containing gas and water, said apparatus comprising:
- a source of ultraviolet radiation;
- a first input associated with said source for receiving water to be exposed to said radiation;
- a first output for said water which has been exposed to said radiation;
- a second input associated with said source for receiving said oxygen containing gas to be exposed to said radiation so that ozone is formed in said gas;
- a second output for said gas containing said ozone;
- a pressure sensor for detecting a drop in pressure at said first output; and
- flow activating apparatus for activating flow of water into said first input when a drop in pressure is detected by said pressure sensor.

19. An appliance capable of receiving an oxygen containing gas and water, said appliance including an apparatus for treating said oxygen containing gas and water, said apparatus comprising:
- a source of ultraviolet radiation;
- a first input associated with said source for receiving water to be exposed to said radiation;
- a first output for said water which has been exposed to said radiation;
- a second input associated with said source for receiving said oxygen containing gas to be exposed to said radiation so that ozone is formed in said gas;
- a second output for said gas containing said ozone;
- a pressure sensor for detecting a drop in pressure at said first output;
- flow activating apparatus for activating flow of water into said first input when a drop in pressure is detected by said pressure sensor; and
- a sensor for detecting ultraviolet radiation produced by said source;

wherein said flow activating apparatus activates the flow of water into said first input only when both said drop in pressure and detection of ultraviolet radiation by said sensor occur.

20. An appliance capable of receiving an oxygen containing gas and water, said appliance including an apparatus for treating said oxygen containing gas and water, said apparatus comprising:
- a source of ultraviolet radiation;
- a first input associated with said source for receiving water to be exposed to said radiation;
- a first output for said water which has been exposed to said radiation;

a second input associated with said source for receiving said oxygen containing gas to be exposed to said radiation so that ozone is formed in said gas;

a second output for said gas containing said ozone;

a tube through which said water flows from said first input to said first output having characteristics which permit said ultraviolet radiation to suppress biological activity in said water, wherein said tube is substantially transparent to said ultraviolet radiation; and a plenum through which gas may be caused to flow from said second input to said second output, said plenum being sized, shaped, and positioned so that when said gas is in said plenum, said gas is exposed to said ultraviolet radiation to a degree sufficient to form ozone in said gas.

21. An appliance capable of receiving an oxygen containing gas and water, said appliance including an apparatus for treating said oxygen containing gas and water, said apparatus comprising:

a source of ultraviolet radiation;

a first input associated with said source for receiving water to be exposed to said radiation;

a first output for said water which has been exposed to said radiation;

a second input associated with said source for receiving said oxygen containing gas to be exposed to said radiation so that ozone is formed in said gas;

a second output for said gas containing said ozone;

a tube through which said water flows from said first input to said first output having characteristics which permit said ultraviolet radiation to suppress biological activity in said water, wherein said tube is formed of tetraflouro-ethylene or quartz; and a plenum through which gas may be caused to flow from said second input to said second output, said plenum being sized, shaped, and positioned so that when said gas is in said plenum, said gas is exposed to said ultraviolet radiation to a degree sufficient to form ozone in said gas.

22. An appliance capable of receiving an oxygen containing gas and water, said appliance including an apparatus for treating said oxygen containing gas and water, said apparatus comprising:

a source of ultraviolet radiation;

a first input associated with said source for receiving water to be exposed to said radiation;

a first output for said water which has been exposed to said radiation;

a second input associated with said source for receiving said oxygen containing gas to be exposed to said radiation so that ozone is formed in said gas; and a second output for said gas containing said ozone, wherein said appliance is one of a refrigerator, a dishwasher a clothes washing machine, a clothes dryer and a clothes washer/dryer.

23. An appliance capable of receiving an oxygen containing gas and water, said appliance including an apparatus for treating said oxygen containing gas and water, said apparatus comprising:

a source of ultraviolet radiation;

a first input associated with said source for receiving water to be exposed to said radiation;

a first output for said water which has been exposed to said radiation;

a second input associated with said source for receiving said oxygen containing gas to be exposed to said radiation so that ozone is formed in said gas;

a second output for said gas containing said ozone; and at least one gas conducting means for conducting said ozone containing gas to a food storage means remote from said appliance.

24. A system for use in an appliance for reducing biological activity, said system comprising:

a source of ultraviolet radiation;

a first input for receiving water to be exposed to said radiation;

a first output for said water which has been exposed to said radiation;

a controller for controlling said source of ultraviolet radiation so that said source is turned on when water begins to flow into said first input, and remains on for a fixed period of time after water ceases to flow into said input, so that water which has flowed into said input but has not yet flowed out of said output is disinfected;

a second input for an oxygen containing gas to be exposed to said radiation so that ozone is formed in said gas; and a second output for said gas containing said ozone.

25. The system of claim 24, wherein said source of ultraviolet radiation is an ultraviolet bulb.

26. The system of claim 24, further comprising:

a housing, said source of ultraviolet radiation being disposed in said housing;

a first plenum through which water may be caused to flow from said first input to said first output, said first plenum being sized, shaped and positioned so that water in said first plenum is exposed to said ultraviolet radiation to a degree sufficient to suppress biological activity in said water; and a second plenum through which said oxygen containing gas may be caused to flow from said second input to said second output, said second plenum being sized, shaped and positioned so that when said gas is in said second plenum, said gas is exposed to said ultraviolet radiation to a degree sufficient to form ozone in said gas.

27. The system of claim 26, wherein said first plenum and said second plenum are cylindrical.

28. The system of claim 27, wherein said first plenum and said second plenum are coaxial.

29. The system of claim 24, further comprising:

a tube through which said water flows from said first input to said first output, said tube having characteristics which permit said ultraviolet radiation to suppress biological activity in said water; and a plenum through which said oxygen containing gas may be caused to flow from said second input to said second output, said plenum being sized, shaped and positioned so that when said gas is in said plenum, said gas is exposed to said ultraviolet radiation to a degree sufficient to form ozone in said gas.

30. The system of claim 29, wherein said tube is substantially transparent to said ultraviolet radiation.

31. The system of claim 30, wherein said tube is formed of tetraflouroethylene.

32. The system of claim 24, further comprising at least one means for conducting said ozone containing gas to a location remote from said appliance.

33. The system of claim 24, further comprising at least one gas conducting means for conducting said ozone containing gas to a food storage means remote from said appliance.

34. The system of claim 24, further comprising at least one water conducting means for conducting said water from said second outlet to a location remote from said appliance.

35. The system of claim 24, further comprising means for introducing ozone into said water.

36. A method for reducing biological activity in an appliance which is capable of receiving an oxygen containing gas and water, comprising:

periodically generating ultraviolet radiation; and exposing said oxygen containing gas and said water in said appliance to said radiation to suppress biological activity in said water and to generate ozone in said oxygen containing gas.

37. The method of claim 36, wherein said exposing of said gas and said water occur simultaneously.

38. The method of claim 36, wherein said gas is air.

39. The method of claim 36, wherein said source of ultraviolet radiation is turned on when water is to be disinfected for use.

40. The method of claim 36, further comprising conducting said ozone containing gas to a location remote from said appliance.

41. The method of claim 36, further comprising conducting said water to a location remote from said appliance.

42. The method of claim 36, further comprising introducing ozone into said water.

43. A method for reducing biological activity in a refrigerator which is capable of receiving an oxygen containing gas and water, comprising:

generating ultraviolet radiation;

exposing said oxygen containing gas and said water in said appliance to said radiation to suppress biological activity in said water and to generate ozone in said gas; and circulating said gas containing said ozone in food containing compartments of said refrigerator.

44. A method for reducing biological activity in a refrigerator which is capable of receiving an oxygen containing gas and water comprising:

generating ultraviolet radiation;

exposing said oxygen containing gas and said water in said appliance to said radiation to suppress biological activity in said water and to generate ozone in said gas; and periodically circulating said gas containing said ozone in food containing compartments of said refrigerator.

45. A method of for reducing biological activity in a refrigerator which is capable of receiving an oxygen containing gas and water comprising:

generating ultraviolet radiation;

exposing said oxygen containing gas and said water in said appliance to said radiation to suppress biological activity in said water and to generate ozone in said gas; and periodically circulating said gas containing said ozone in food containing compartments of said refrigerator, wherein said gas is circulated for a relatively short period of time once every day.

46. A method for reducing biological activity in a refrigerator which is capable of receiving an oxygen containing gas and water comprising:

generating ultraviolet radiation;

exposing said oxygen containing gas and said water in said appliance to said radiation to suppress biological activity in said water and to generate ozone in said gas; and periodically circulating said gas containing said ozone in food containing compartments of said refrigerator, wherein said gas is circulated at a time of day when said refrigerator is not generally in use.

47. A method for reducing biological activity in a refrigerator which is capable of receiving an oxygen containing gas and water comprising:

generating ultraviolet radiation;

exposing said oxygen containing gas and said water in said appliance to said radiation to suppress biological activity in said water and to generate ozone in said gas; and periodically circulating said gas containing said ozone in food containing compartments of said refrigerator, wherein said gas is circulated at a time of day when said time of day is at least one of during sleep of individuals using said refrigerator and during periods of time when said individuals are working.

48. A method for reducing biological activity in a refrigerator which is capable of receiving an oxygen containing gas and water comprising:

generating ultraviolet radiation;

exposing said oxygen containing gas and said water in said appliance to said radiation to suppress biological activity in said water and to generate ozone in said gas; and periodically circulating said gas containing said ozone in food containing compartments of said refrigerator, wherein said gas is circulated at a time of day when said time of day is at least one of during sleep of individuals using said refrigerator and during periods of time when said individuals are working for a period of time between thirty seconds and two hours, once every day.

49. A method for reducing biological activity in an appliance which is capable of receiving an oxygen containing gas and water, comprising:

generating ultraviolet radiation; and exposing said oxygen containing gas and said water in said appliance to said radiation to suppress biological activity in said water and to generate ozone in said gas, wherein said source of ultraviolet radiation is turned on when water is to be disinfected for use and said gas is not circulated when said source of ultraviolet radiation is turned on when water is to be disinfected for use.

50. A method for reducing biological activity in an appliance which is capable of receiving an oxygen containing gas and water, comprising:

generating ultraviolet radiation;

exposing said oxygen containing gas and said water in said appliance to said radiation to suppress biological activity in said water and to generate ozone in said gas; and conducting said ozone containing gas to a food storage means remote from said appliance.

* * * * *